United States Patent [19]

Lada et al.

[11] 4,061,750

[45] Dec. 6, 1977

[54] ANTIMICROBIAL COMPOSITION

[75] Inventors: Arnold Lada, Monmouth Beach; Alfonso N. Petrocci, Glen Rock, both of N.J.; Harold A. Green, Havertown, Pa.; John J. Merianos, Jersey City, N.J.

[73] Assignee: Kewannee Industries, Bryn Mawr, Pa.

[21] Appl. No.: 722,390

[22] Filed: Sept. 13, 1976

[51] Int. Cl.² .......................... A01N 9/22; A01N 9/24
[52] U.S. Cl. ................................. 424/249; 424/325; 424/331; 424/333; 424/334

[58] Field of Search ............... 424/331, 334, 249, 333, 424/325

[56] References Cited

U.S. PATENT DOCUMENTS 2,990,266  6/1961  Eden ........................................ 71/2.7
3,515,671  6/1970  Adams et al. .......................... 252/54

Primary Examiner—Leonard Schenkman
Attorney, Agent, or Firm—Arthur A. Jacobs

[57] ABSTRACT

An antimicrobial synergistic mixture of halogenated carbonyl compounds with condensation products of formaldehyde and ethanolamine.

6 Claims, No Drawings

ANTIMICROBIAL COMPOSITION

This invention relates to synergistic mixtures of two types of antimicrobial compounds which are well known in the art.

One type of compound has the structural formula:

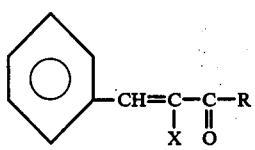

in which X represents a halogen and R represents either hydrogen, alkyl, aryl or cycloalkyl and contains no more than 8 carbon atoms. The synthesis of this class of compounds and some of its antimicrobial properties has been described in U.S. Pat. No. 3,515,671, which is incorporated herein by reference. Exemplifying this class of compounds is α-bromocinnamaldehyde wherein X represents Br, and R represents hydrogen.

The second type of compound is exemplified by a 1:1 molar condensation product formed by the reaction of formaldehyde and ethanolamine. Methods of synthesizing this product and some of its properties are described in U.S. Pat. No. 2,990,266 and in German Pat. Nos. 1,148,706 and 1,812,054, which are also incorporated by reference. The condensation product appears to be substantially N, N', N"-tris-(2-hydroxyethyl)-hexahydrotriazine.

In accordance with the present invention, it has now been discovered that certain mixtures of the aforesaid compounds, within a narrow range of proportions, have antimicrobial properties that are far more potent than the sum of the individual contributions of each component. Such compounds have been found to be excellent preservatives for metal-working fluids and the like, such as cutting and grinding fluids, lubricating fluids, cooling and washing fluids, etc., as described in the aforementioned U.S. Pat. No. 3,515,671. They may also be used in many other applications where antimicrobial preservative action or other antimicrobial action is desired. In this respect, they may, for example, be used in water treatment to control the proliferation of microorganisms in cutting oils, cosmetics, textiles, leather, hard surfaces, and many other products or processes where the growth of microorganisms, particularly Gram-negative organisms (such as Pseudomnas aerugnosa) and fungi (such as Aspergillus niger,) present problems.

In the following described tests, the synergistic interaction between α-bromocinnamaldehyde and N, N', N"-tris-(2-hydroxyethyl)-hexahydrotriazine (which is the designation hereinafter used for the condensation product) was demonstrated by the same mathematical treatment of data used by Kull, Eisman, Sylwestrowicz and Mayer and described in "Applied Microbiology" 9, 538-541 (1946).

According to the aforementioned Kull et al method, the quantities of pure materials and their quantities in various mixtures are compared when the pure materials and the mixtures reach the same end point or produce the same microbiological effect.

According to this method, synergism is demonstrated when $$\frac{Q_A}{Q^\circ_A} + \frac{Q_B}{Q^\circ_B} < 1$$

In this formula $Q^\circ_A$ and $Q^\circ_B$ are the minimum quantities of pure α-bromocinnamaldehyde and N, N', N"-tris-(2-hydroxyethyl)-hexahydrotriazine which are respectively required to bring about the complete inhibition of microbial growth of any species, and $Q_A$ and $Q_B$ are their respective quantities in the mixtures which also cause the complete inhibition of growth of the same microbial species.

Growth inhibition tests were performed on pure α-bromocinnamaldeyde, pure N, N', N"-tris-(2-hydroxyethyl)-hexahydrotriazine, and mixtures of the two in various ratios, for the purpose of determining their bacteriastatic and fungistatic activities, as follows:

To a test tube holding 10 ml. of sterile nutrient broth, containing the compound or mixture to be tested in various concentrations, there was added 0.1 ml. of a 24-hour nutrient broth culture of Pseudomonas aeruginosa bacteria so that the contents had a concentration of $1–10 \times 10^6$ organisms per ml.

The bacteria were incubated at 37° C. for 72 hours and then the presence or absense of macroscopic bacterial growth was observed. The minimum concentration of either the pure compounds or mixtures which prevented macroscopic growth was designated as the "Minimum Inhibitory Level" (MIL).

To a test tube holding 10 ml. of a sterile sabouraddextrose broth, containing the compound or mixture to be tested, there was added 0.1 ml. of a saline suspension of Aspergillus niger so that the contents had a concentration of $0.5–1.0 \times 10^6$ spores of fungi per ml.

The fungi were incubated at 25° C. for 14 days and the presence or absence of macroscopic growth at the end of 7 and 14 days, respectively, were observed. The minimum concentration of pure compound or mixture which prevented the macroscopic growth was designated as the MIL.

Table I lists the "Minimum Inhibitory Levels" (MIL) in parts per million of pure α-bromocinnamaldehyde, pure 1:1 molar condensation product of formaldehyde and ethanolamine which is presumed to be N, N', N"-tris-(2-hydroxyethyl)-hexahydrotriazine, and mixtures of the two pure compounds in various ratios, all tested against the organisms Pseudomonas aeruginosa and Aspergillis niger.

Table II lists the actual concentration of each component in each test at the "Minimum Inhibitory Level."

Table III lists the value of the sum $$\frac{Q_A}{Q^\circ_A} + \frac{Q_B}{Q^\circ_B}$$

for each test at the "Minimum Inhibitory Level."

Table III demonstrates unequivocally that there is synergism in the antimicrobial activity of α-bromocinnamaldehyde and the 1:1 molar condensation product of formaldehyde and ethanolamine which is presumed to be N, N', N"-tris-(2-hydroxyethyl)-hexahydrotriazine.

The ratio of components at which synergism is displayed against Pseudomonas aeruginosa is from about 1:7 to about 1:9 parts of α-bromocinnamaldehyde relative to the condensation product, and the ratio of components at which synergism is displayed against Aspergillis Niger is about 1:7 parts of α-bromocinnamaldehyde relative to the condensation product.

Table I

| Minimum Inhibitory Levels In Parts Per Million | | |
|---|---|---|
| | Pseudomonas Aeruginosa | Aspergillis Niger |
| α-Bromocinnamaldehyde | 70 ($Q°_A$) | 45 ($Q°_A$) |
| Condensation Product | 400 ($Q°_B$) | 750 ($Q°_B$) |
| 1 Part | | |
| α-Bromocinnamaldehyde 7 Parts Condensation Product 1 Part | 150 | 200 |
| α-Bromocinnamaldehyde 9 Parts Condensation Product 1 Part | 200 | 550 |
| α-Bromocinnamaldehyde 11 Parts Condensation Product | 300 | |

Table II

| Concentrations Of Components In Parts Per Million At The Minimum Inhibitory Level | | | | |
|---|---|---|---|---|
| | Pseudomonas Aeruginosa | | Aspergillis Niger | |
| 1:7 Ratio | | | | |
| α-Bromocinnamaldehyde | 18.75 | ($Q_A$) | 25.0 | ($Q_A$) |
| Condensation Product | 131.25 | ($Q_B$) | 175.0 | ($Q_B$) |
| 1:9 Ratio | | | | |
| α-Bromocinnamaldehyde | 20.0 | ($Q_A$) | 55.0 | ($Q_A$) |
| Condensation Product | 180.0 | ($Q_B$) | 495.0 | ($Q_B$) |
| 1:11 Ratio | | | | |
| α-Bromocinnamaldehyde | 25.0 | ($Q_A$) | | |
| Condensation Product | 275.0 | ($Q_B$) | | |

Table III

Values for the sum $\frac{Q_A}{Q°_B} + \frac{Q_B}{Q°_B}$

| | Pseudomonas Aeruginosa | Aspergillis Niger |
|---|---|---|
| 1:7 Ratio | 0.60 | .79 |
| 1:9 Ratio | 0.74 | >1.0 |
| 1:11 Ratio | >1.0 | |

The invention claimed is:

1. An antimicrobial composition consisting essentially of a mixture of α-bromocinnamaldehyde and a condensation product of formaldehyde and ethanolamine wherein the formaldehyde and the ethanolamine are reacted in a molar proportion of about 1:1, the α-bromocinnamaldehyde and the condensation product being in a proportion, in parts by weight, of about 1:7 to about 1:9.

2. A method of inhibiting the growth of bacteria which comprises applying a bacteria-inhibiting effective amount of the composition of claim 1 to said bacteria.

3. The method of claim 2 wherein the bacteria is gramnegative.

4. The method of claim 3 wherein the bacteria is Pseudomonas aeruginosa.

5. A method of inhibiting the growth of fungi which comprises applying a fungi-inhibiting effective amount of the composition of claim 1 to said fungi, the proportion of the halogenated compound to the condensation product being about 1:7 parts by weight.

6. The method of claim 5 wherein the fungi is Aspergillis niger.

* * * * *